United States Patent [19]

Leone-Bay et al.

[11] Patent Number: 4,721,822

[45] Date of Patent: Jan. 26, 1988

[54] PROCESS FOR PREPARING 2,6-DICHLOROTOLUENE

[75] Inventors: Andrea Leone-Bay, Ridgefield, Conn.; Peter E. Timony, Valley Cottage; Laurel Glaser, Buchanan, both of N.Y.

[73] Assignee: Stauffer Chemical Company, Westport, Conn.

[21] Appl. No.: 862,934

[22] Filed: May 14, 1986

[51] Int. Cl.[4] .............................................. C07C 17/12
[52] U.S. Cl. ...................................... 570/201; 570/211
[58] Field of Search ................................ 570/201, 211

[56] References Cited

U.S. PATENT DOCUMENTS 4,006,195  2/1977  Gelfand ............................... 570/210

FOREIGN PATENT DOCUMENTS 133000  11/1901  Fed. Rep. of Germany ...... 570/210
 39084  of 1971  Japan .................................... 570/210
313207   6/1929  United Kingdom ................ 570/201

*Primary Examiner*—J. E. Evans
*Attorney, Agent, or Firm*—Hensley M. Flash

[57] ABSTRACT

Liquid para-toluenesulfonyl chloride is reacted with chlorine gas at elevated temperatures in the presence of a catalytic amount of a Lewis acid catalyst, preferably antimony trichloride. Sulfuric acid is added then the reaction mixture is heated and subsequently cooled to about room temperature. Ammonium hydroxide is added then the reaction mixture is distilled to yield a substantially pure 2,6-dichlorotoluene.

7 Claims, No Drawings

PROCESS FOR PREPARING 2,6-DICHLOROTOLUENE

BACKGROUND OF THE INVENTION

1. Field of the Invention

This invention relates to a process for preparing 2,6-dichlorotoluene, and more particularly to a process wherein liquid para-toluenesulfonyl chloride is reacted wtih chlorine gas in the presence of a catalyst.

2. Related Information

Dichlorinated toluenes are important intermediates in the preparation of pharmaceuticals, dyes, pigments, rubber chemicals and other organic compounds. 2,6-dichlorotoluene is especially useful as an intermediate in the preparation of herbicides.

U.S. Pat. No. 4,006,195 issued to Gelfand, Feb. 1, 1977, discloses an improved process for the catalytic production of 2,4-dichlorotoluene by reacting liquid parachlorotoluene with chlorine in the presence of an antimony trichloride catalyst at a temperature from about 0° C. to about 100° C. and especially from about 20° C. to about 70° C. The reaction product is treated with anhydrous ammonia then the catalyst is removed by filtration prior to distillation which yields substantially pure 2,4-dichlorotoluene. This process neither discloses the preparation of 2,6-dichlorotoluene nor the use of liquid para-toluenesulfonyl chloride as a reagent.

Japanese Patent, Jpn. Kokai Tokkyo Koho JP No. 60/16965 A2 (85/16965), Jan. 28, 1985, Appl. 83/124691, July 11, 1983 cited in Chemical Abstracts as CA 103(3):22277t discloses the dechlorination of tricholoro-paratoluenesulfonic acid in sulfuric acid with cuprous or cupric compounds. Desulfonation yielded 98.5% 2,6-dichlorotoluene. This reference neither discloses the use of liquid paratoluenesulfonyl chloride and ammonium hydroxide nor the use of antimony trichloride, or ferric chloride catalysts.

PRODUCTION OF 2,3,6-TRICHLOROBENZOIC ACID BY LIQUIDPHASE CATALYTIC OXIDATION OF 2,3,6-TRICHLOROTOLUENE, F.F. Shcherbina, D. N. Tmenov, T. V. Lysukho, and N. P. Belous, Institute of Physicoorganic Chemistry and Coal Chemistry, Petrochemical Branch, Academy of Sciences of the Ukranian SSR, pages 2076–2078, translated from Zhurnal Prikladnoi Khimii, Vol. 53, No. 12, pp 2737–2740, December, 1980, discloses that para-toluenesulfonic acid and antimony trichloride in chloroform was heated to 70°–80° C. with agitation while chlorine was passed through the reaction mixture. After the solvent was distilled, 75% sulfuric acid was boiled with the residue which was later extracted with toluene. The toluene extract was washed with 5% alkali solution then the toluene was distilled off. The resulting product contained 1.4% dichlorotoluenes, 0.7% tetrachlorotoluenes, and 97.9% 2,3,6-trichlorotoluene. This reference primarily discloses the preparation of trichlorotoluene and utilizes a chloroform solvent in the catalyzed reaction.

W. Davis et al., *J. CHEM. SOC.* 119, 853 (1921), THE CUMULATIVE EFFECT OF THE CHLORINE ATOM AND THE METHYL AND SULFONYL CHLORIDE GROUPS ON SUBSTITUTION IN THE BENZENE NUCLEUS. PART 1. discloses the preparation of 2,6-dichloro-para-toluenesulfonyl chloride by chlorinating a fused mixture of 2-chloro-para-toluenesulfonyl chloride and antimony chloride at 67°–75° C. for 2 hours. This reference neither describes the use of para-toluenesulfonyl chloride nor the use of sulfuric acid and ammonium hydroxide.

U.S. Pat. No. 3,470,151 issued to Doyle et al., Sept. 30, 1969, discloses the preparation of 2,6-dichlorotoluene according to the procedure of W. Davis et al., J. Chem. Soc., 119, 853 (1921). In this preparation, a mixture of 3,5-dichloro-4-methylbenzenesulfonyl chloride and 50% sulfuric acid was refluxed until the solution became homogeneous. The solution was then distilled with superheated steam for 5 hours and the distillate extracted with chloroform. The extracts were washed with water and dried with calcium chloride, the filtrate being evaporated to remove the solvent. Distillation of the residual oil gave 2,6-dichlorotoluene. This reference neither describes the catalyzed chlorination of liquid para-toluenesulfonyl chloride nor the treatment with ammonium hydroxide.

SUMMARY OF THE INVENTION

This invention is a process for preparing 2,6-dichlorotoluene comprising: (a) reacting liquid paratoluenesulfonyl chloride and chlorine gas in the absence of a solvent and in a molar ratio of the chloride to gas from about 0.5:1 to about 1.5:1 at a temperature from about 70° C. to about 100° C. in the presence of a catalytic amount of a Lewis acid catalyst; (b) adding sulfuric acid to the reaction mixture of step (a) then heating the mixture; (c) cooling the reaction mixture of step (b) to about room temperature then adding at least one equivalent, based on the added sulfuric acid, of ammonium hydroxide to yield 2,6-dichlorotoluene. This process can further include heating the reaction mixture of step (b) to a temperature from about 100° C. to about 150° C. for about 20 hours to about 48 hours prior to step (c). Distilling the reaction mixture resulting form the final step of this process yeidls substantially pure 2,6-dichlorotoluene.

The catalyzed chlorination of liquid para-chlorotoluene and the subsequent treatment of the reaction product with anhydrous ammonia has been shown by Gelfand to yield substantially pure 2,4-dichlorotoluene. However, none of the references disclose the process of this invention described above for preparing 2,6-dichlorotoluene.

An object of this invention is to provide such a method for preparing 2,6-dichlorotoluene starting from the catalyzed chlorination of liquid para-toluenesulfonyl chloride in the absence of a solvent.

Other objects and advantages of the present inention are described elsewhere within this specification.

DETAILED DESCRIPTION OF THE INVENTION

The process of the present invention is carried out by contacting para-toluenesulfonyl chloride with chlorine in the presence of a catalytic amount of a Lewis acid catalyst. This catalyst is selected from the group consisting of antimony trichloride, ferric chloride, boron trichloride, nickel chloride, magnesium chloride and mixtures thereo. It is expected that other Lewis acids can catalyze this reaction, therefore the above listing is merely exemplary. A particularly preferred catalyst is antimony trichloride. antimony pentachloride is generally present in a commercial composition of antimony trichloride, and antimony trichloride can react in the chlorination process to form trichloride and pentachloride in this process would be inappropriate. therefore, the use of the term antimony trichloride includes a composition which can comprise antimony pentachloride.

A preferred catalyst useful in the present invention is selected from the group consisting of ferric chloride, antimony trichloride and mixtures thereof. Only a small amount of catalyst need be present in the reaction mxiture. Amounts as low as 0.01 moles of the catalyst can be useful, and amounts above 0.3 mole should not offer any added advantage. Therefore, a preferred range is from about 0.01 to about 0.3 moles with 0.1 mole being especially preferred.

In this process, the para-toluenesulfonyl chloride is a liquid and the chlorine gas is bubbled through this liquid mixture of the para-toluenesulfonyl chloride and the catalyst in the absence of a solvent. Sufficient chlorine gas is bubbled into the reaction mixture to ensure that the molar ratio of the para-toluenesulfonyl chloride to the chlorine gas ranges from about 0.5:1 to about 1.5:1. Weights of chlorine gas close to the stoichiometric ratio are preferred, i.e. a olar ratio of the para-toluenesulfonyl chloride to chlorine gas of about 1:1 is preferred.

The catalyzed chlorination reaction is carried out at elevated temperatures. This temperature can range from about 70° C. to about 100° C. with a temperature from about 75° C. to about 85° C. being preferred, and a temperature of about 80° C. being especially preferred. This catalyzed chlorination reaction is carried out in the absence of a solvent. The use of temperatures above 100° C. or superatmospheric pressure is discouraged because there might be a tendency for by-products to be formed, e.g., side chain chlorinated by-products, etc.

The product of the catalyzed chlorination is not isolated. sufuric acid is added to this chlorinated reaction mixture. A preferred concentration of sulfuric acid is about 75 weight percent and this acid can be added in an amount ranging from about 1 mole to about 10 moles. After addition of the acid, the resulting mixture is heated, preferably to a temperature from about 100° C. to about 150° C. for about 20 hours to about 48 hours. It is particularly preferred that this reaction mixture be heated to about 130° C. for about 24 hours.

After this heating step, the reaction mixture is cooled to about room temperature, then ammonium hydroxide is added in an amount that is at least one equivalent, based on the added sulfuric acid. 2,6-dichlorotoluene can then be recovered from this reaction mixture by various techniques. In a particular technique, the catalyst can be removed by separation or filtration, then the 2,6-dichlorotoluene fraction can be separated by fractional distillation or other known techniques to yeild substantially pure 2,6-dichlorotoluene.

In a particular embodiment of this invention the catalyst is 0.1 mole of antimony trichloride and the catalyzed chlorination is carried out at a temperature of about 80° C. Sulfuric acid having a concentration of 75 weight percent is added to the reaction mixture which is then heated to about 130° C. for about 24 hours, then ammonium hydroxide is added dropwise after the reaction mixture is cooled. Distillation of the reaction mixture yields substantially pure 2,6-dichlorotoluene.

The following experiments describe various embodiments of the invention. Other embodiments will be apparent to one of ordinary skill in the art from a consideration of this specification or practice of the invention disclosed herein. It is intended that the specification and experiments be considered as exemplary only, with the true scope and spirit of the invention being indicated by the claims which follow the experiments.

EXPERIMENT I

The following procedure describes the process of this invention for preparing 2,6-dichlorotoluene.

Chlorine gas was bubbled into a molten mixture of 4-toluenesulfonyl chloride (20 g., 105 mM) and antimony trichloride (100 mg, 4 mM) at such a rate as to maintain a reaction temperature of 80° C. When the theoretical amount of chlorine has been taken up, 75% aqueous sulfuric acid (50 mL) was added to the reaction mixture. The resulting dark solution was heated at 130° C. for 40 hours and poured into water (100 mL). This aqueous mixture was neutralized by the slow addition of ammonium hydroxide, followed by ether extraction. The ether extracts were washed with water and brine, dried over anhydrous sodium sulfate and distilled at reduced pressure to give 2,6-dichlorotoluene (8.4 g, 50 wt. %).

EXPERIMENTS II-III

The two following procedures represent failed attempts to prepare 2,6-dichlorotoluene.

1. A mixture of 2,6-dichloro-4-toluenesulfonyl chloride (4 g, 15.5 mM) and 75% aqueous sulfuric acid (10 mL) was heated at 130° C. for 40 hours. The reaction mixture was cooled and extracted with toluene. The toluene extracts were washed first with 5% aqueous sodium hydroxide, followed by water and finally brine. Distillation of the toluene left a residue which did not contain 2,6-dichlorotoluene.

2. A mixture of 2,6-dichloro-4-toluenesulfonyl chloride (10 g, 38.8 mM and 75% aqueous sulfuric acid (25 mL) was heated at 130° C. for 40 hours. The reaction mixture was diluted with water (50 mL) and steam distilled to give a clear distillate (50 mL). This distillate was extracted with ethyl acetate. The ethyl acetate extracts were washed with water, then brine and concentrated in vacuo to give a yellow liquid which did not contain 2,6-dichlorotoluene.

What is claimed is:

1. A process for preparing 2,6-dichlorotoluene comprising:
    (a) reacting liquid para-toluenesulfonyl chloride and chlorine gas in the absence of a solvent and in a molar ratio of the chloride to gas from about 0.5:1 to about 1.5:1 at a temperature from about 70° C. to about 100° C. in the presence of a catalytic amount of a Lewis Acid catalyst;
    (b) adding sulfuric acid to the reaction mixture of step (a) then heating the mixture; and
    (c) cooling the reaction mixture of step (b) to about room temperature then neutralizing by adding at least one equivalent, based on the added sulfuric acid, of ammonium hydroxide to yield 2,6-dichlorotoluene.

2. The process of claim 1 wherein the reaction mixture of step (b) is heated to a temperature from about 100° C. to about 150° C. for about 20 hours to about 48 hours prior to step (c).

3. The process of claim 2 wherein the catalyst is selected from the group consisting of antimony trichloride, ferric chloride, boron trichloride, nickel chloride, magnesium chloride and mixtures thereof.

4. The process of claim 3 wherein the catalyst is antimony trichloride present from about 0.01 to about 0.3 moles.

5. The process of claim 3 wherein step a) is conducted at a temperature from about 75° C. to about 85° C.

6. The process of claim 1 further comprising distilling the reaction mixture of step (c) to yield substantially pure 2,6-dichlorotoluene.

7. The process of claim 1 wherein the catalyst is about 0.1 mole of antimony trichloride, the reaction of step (a) is conducted at a temperature of about 80° C., the reaction mixture of step (b) is heated to about 130° C. for about 24 hours, the concentration of the sulfuric acid is 75 weight percent and the ammonium hydroxide is added at a rate sufficient to control the exothermic reaction.

* * * * *

UNITED STATES PATENT AND TRADEMARK OFFICE
CERTIFICATE OF CORRECTION

PATENT NO. : 4,721,822

DATED : January 26, 1988

INVENTOR(S) : Andrea Leone-Bay et al.

It is certified that error appears in the above-identified patent and that said Letters Patent is hereby corrected as shown below:

In column 2, the last two lines should read:

--- chlorination process to form the pentachloride, hence a distinction between the trichloride and pentachloride in this process would be inappropriate. Therefore, ---

Signed and Sealed this

Third Day of January, 1989

Attest:

DONALD J. QUIGG

*Attesting Officer*  *Commissioner of Patents and Trademarks*